United States Patent
Lievois et al.

(10) Patent No.: US 6,292,756 B1
(45) Date of Patent: Sep. 18, 2001

(54) NARROW BAND INFRARED WATER FRACTION APPARATUS FOR GAS WELL AND LIQUID HYDROCARBON FLOW STREAM USE

(75) Inventors: John S. Lievois; Roberto M. Lansangan; George J. Rodger, all of Houston; Arnold Del Toro, Stafford, all of TX (US)

(73) Assignee: Premier Instruments, Inc., Houston, TX (US)

( * ) Notice: Subject to any disclaimer, the term of this patent is extended or adjusted under 35 U.S.C. 154(b) by 0 days.

(21) Appl. No.: 09/531,243

(22) Filed: Mar. 21, 2000

Related U.S. Application Data

(63) Continuation-in-part of application No. 09/031,098, filed on Feb. 26, 1998, now Pat. No. 6,076,049.

(51) Int. Cl.$^7$ .............................. G01F 5/00; G01N 22/00
(52) U.S. Cl. ..................... 702/50; 702/100; 73/61.44; 73/861.04; 324/637
(58) Field of Search .............................. 702/100, 45, 49, 702/50, 179; 73/61.44, 861.04; 250/256, 339.1, 338.5, 343; 324/637, 640

(56) References Cited

U.S. PATENT DOCUMENTS

| | | | |
|---|---|---|---|
| 3,783,284 | 1/1974 | McCormack | 250/339 |
| 4,171,918 | 10/1979 | Mactaggart | 356/408 |
| 4,265,535 | 5/1981 | Pitt et al. | 356/70 |
| 4,490,609 | 12/1984 | Chevalier | 250/269 |
| 4,492,862 | 1/1985 | Grynberg et al. | 250/255 |
| 4,628,204 | 12/1986 | Maes | 250/343 |
| 4,649,281 | 3/1987 | Schmitt et al. | 250/574 |
| 4,674,879 | 6/1987 | Gregorig et al. | 356/301 |
| 4,809,543 | 3/1989 | Baillie et al. | 73/61.1 |
| 4,947,129 | 8/1990 | Helms et al. | 324/640 |
| 4,994,671 | 2/1991 | Safinya et al. | 250/255 |
| 5,035,581 | 7/1991 | McGuire et al. | 417/36 |
| 5,067,345 | 11/1991 | Mougne | 76/61.1 |
| 5,105,085 | 4/1992 | McGuire et al. | 250/343 |
| 5,107,118 | 4/1992 | Murray, Jr. et al. | 250/339 |
| 5,253,198 | 10/1993 | Birge et al. | 365/106 |
| 5,266,800 | 11/1993 | Mullins | 250/256 |

(List continued on next page.)

FOREIGN PATENT DOCUMENTS

2022933 C1    11/1994   (RU).

Primary Examiner—Kamini Shah
(74) Attorney, Agent, or Firm—Akin, Gump, Strauss, Hauer & Feld, L.L.P.

(57) ABSTRACT

A narrow band infrared water fraction meter detects a full water cut range of a liquid hydrocarbon flow stream and a flow stream of a gas well. The water fraction meter includes a light source probe for irradiating the flow stream with a narrow band of infrared light and a light detector probe for sensing attenuation of infrared light passed through the flow stream. For a narrow band of infrared light of a predetermined wavelength, there is a substantial difference in the absorption of infrared radiation between the gas and water content of a flow stream of a gas well. At such a wavelength, the narrow band of infrared light is substantially transmitted through gas content and liquid hydrocarbon content of the flow stream and substantially absorbed by water content of the flow stream. The water fraction meter thus differentiates water by treating liquid hydrocarbon like gas. Injection of corrosion/hydrate inhibiting chemicals into the flow stream can be controlled based on the attenuation of infrared light detected by the water fraction meter. In the case of a liquid hydrocarbon flow stream, the infrared light is substantially transmitted through its liquid hydrocarbon phase and substantially absorbed by its water phase. The water fraction meter also measures a water fraction of a multi-phase flow stream. The emitted infrared light is substantially transmitted through a first set of phases of the flow stream and substantially absorbed by a second set of phases of the flow stream.

20 Claims, 12 Drawing Sheets

U.S. PATENT DOCUMENTS

| | | | |
|---|---|---|---|
| 5,331,156 | 7/1994 | Hines et al. | 250/256 |
| 5,369,368 | 11/1994 | Kassen et al. | 324/632 |
| 5,418,614 | 5/1995 | Brost et al. | 356/434 |
| 5,452,076 | 9/1995 | Schopper et al. | 356/128 |
| 5,567,318 | 10/1996 | Beall | 210/691 |
| 5,576,974 | 11/1996 | Marrelli et al. | 364/554 |
| 5,654,551 | 8/1997 | Watt et al. | 250/356 |
| 5,689,540 | 11/1997 | Stephenson et al. | 378/53 |
| 5,870,926 | 2/1999 | Saito et al. | 73/73 |
| 6,076,049 * | 6/2000 | Lievois et al. | 702/100 |

* cited by examiner

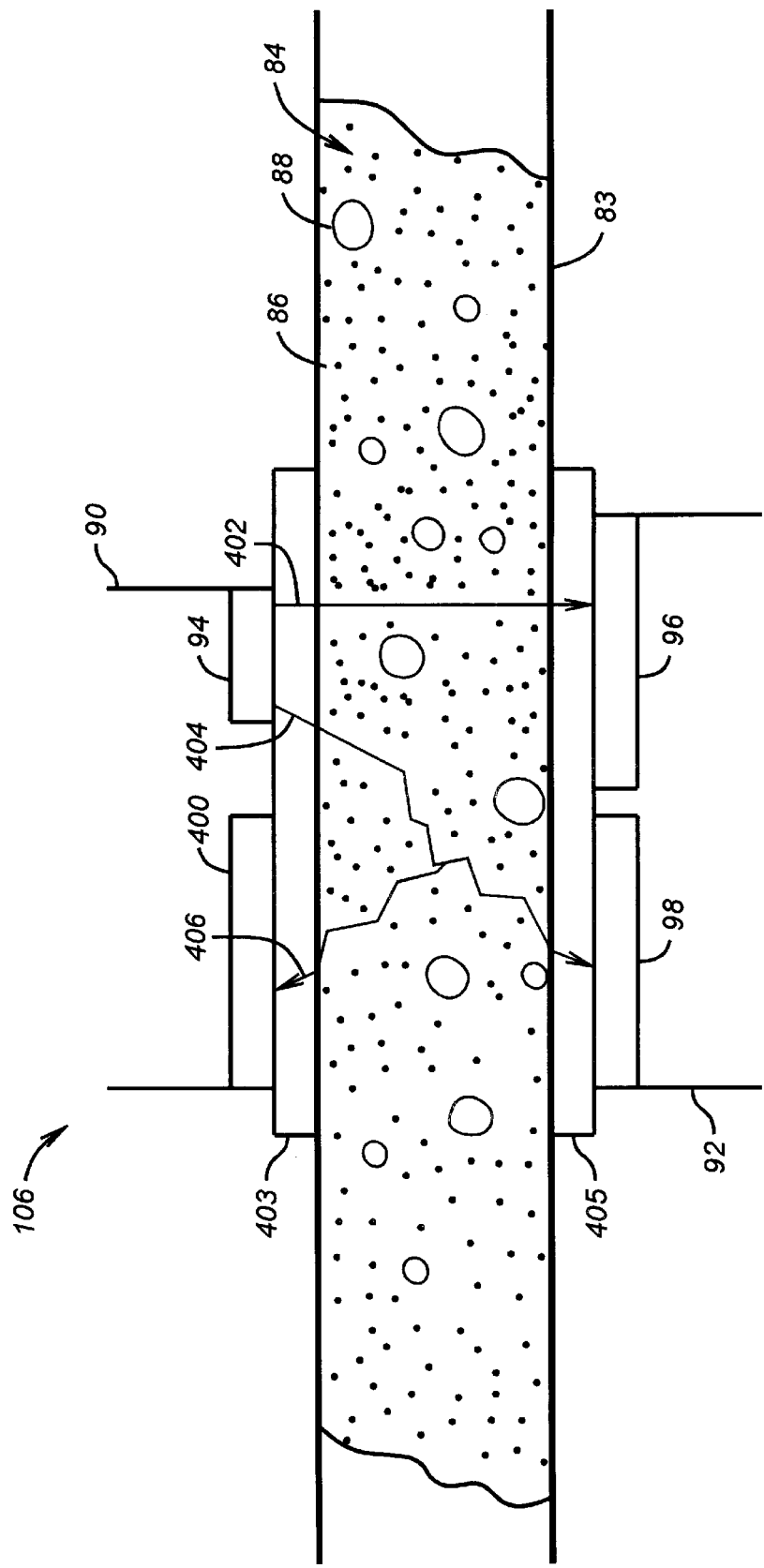

NARROW BAND INFRARED WATER FRACTION APPARATUS FOR GAS WELL AND LIQUID HYDROCARBON FLOW STREAM USE

RELATED APPLICATIONS

This application is a continuation-in-part of U.S. patent application Ser. No. 09/031,098, filed Feb. 26, 1998 entitled NARROW BAND INFRARED WATER CUT METER, by John S. Lievois, Roberto M. Lansangan and Mark E. Sudberry, now U.S. Pat. No. 06,076,049 which is hereby incorporated by reference in its entirety for all purposes.

BACKGROUND OF THE INVENTION

1. Field of the Invention

The present invention generally relates to water fraction meters or moisture content meters, and more particularly to a narrow band infrared water fraction meter for gas well and liquid hydrocarbon flow stream use.

2. Description of the Related Art

Natural gas wells often produce water along with the natural gas during normal production. The water is resident in the reservoir and frequently accompanies the natural gas as it flows up to the surface production equipment. Normally, the fraction of the overall flow stream that is comprised of water is small on a volume percentage basis but this value can change. The entrained water can lead to pipeline corrosion and gas hydrate formation, which can actually plug the pipeline. Operators periodically measure the water fraction of the gas well to insure that the corrosion inhibition and hydrate inhibition schemes (typically chemical injection) are adequately sized. The water fraction measurement is also a indicator of the general health of the well.

Conventional methods for determining a natural gas well's water fraction are either inaccurate or expensive. A common method for gauging the water content as it relates to corrosion is to place test metal coupons in the pipeline for an extended period of time. The coupon is then analyzed for corrosive degradation, and an average corrosion rate is determined. This technique allows for an average water content determination, but to handle real life variations, operators have to design the chemical injection rate of the corrosion inhibitor for the estimated highest instantaneous water fraction. This conservative approach is very inefficient and can result in excess use of inhibition chemicals, which can cost tens of thousands of dollars per well per year.

Another common method of water fraction measurement involves separation of the water and natural gas with relative measurement of each stream. These separators can give better real time data (at least on a daily average basis), but the equipment can be large and prohibitively expensive for individual wells.

Online sensors that measure the relative concentrations of water and gas without requiring separation of the two phases are the preferred method for optimizing chemical injection. While there are a few sensor technologies currently being employed as water fraction or moisture content analyzers, most are either too expensive for individual wellhead application or they are very susceptible to dissolved mineral content in the water phase.

Examples of water fraction or moisture content analyzers are described in Kassen et al., U.S. Pat. No. 5,369,368, Helms et al. U.S. Pat. No. 4,947,129, Mactaggart, U.S. Pat. No. 4,171,918, Saito et al., U.S. Pat. No. 5,870,926, Murray Jr. et al., U.S. Pat. No. 5,107,118, Lew et al., U.S. Pat. No. 4,785,245, Stephenson et al., U.S. Pat. No. 5,689,540, and Mougne, U.S. Pat. No. 5,067,345. Kassen et al. and Helms et al. describe examples of devices which use microwave energy and its measured transmission or reflection through the target media to determine the water content or cut. In both cases, a phase shift indicates a change in water content when compared to a reference condition. Lew et al. describes a water cut meter that employs nuclear magnetic resonance (NMR) analysis. In this device, traditional pulse NMR techniques are used to determine the percentage of one component of a multiphase fluid (oil, water, gas, and soil particles) flowing in a pipeline. Stephenson et al. describes a water fraction meter that uses X-rays. An X-ray generator provides a continuous bremsstrahlung photon spectrum to a pipeline stream containing a mixture of oil, water, and gas. Photons from multiple detectors are measured, and an algorithm is used to determine water cut. Mougne describes an apparatus for calculating bulk water in crude oil or steam using a capacitance measurement. It is an in-line probe capable of measuring "bulk" capacitance with a way to calculate the water content based on the measured signal.

Mactaggart, Saito et al., and Murray Jr. et al. all describe infrared based moisture or water content analyzers. Mactaggart and Saito et al. describe devices for determining moisture content of a material by measuring the relative reflectance at two infrared wavelengths. Murray Jr. et al. describes an infrared device that measures transmission of infrared energy at a frequency in the 3700–4000 $cm^{-1}$ range. A reference measurement is then made with a "dry" sample, and the ratio of the values is an indication of the moisture content.

SUMMARY OF THE INVENTION

Briefly, a narrow band infrared water fraction meter measures a water fraction of a flow stream of a gas well or a water fraction of a liquid hydrocarbon flow stream. The water fraction meter includes a light source probe for irradiating the flow stream with a narrow band of infrared light and a light detector probe for sensing or detecting attenuation of the infrared light passed through the flow stream. For a narrow band of infrared light of a predetermined wavelength, there is a substantial difference in the absorption of infrared radiation between gas and water content of a flow stream of a gas well. At such a wavelength, the narrow band of infrared light is substantially transmitted through a gas phase and a liquid hydrocarbon (e.g., condensate) phase of the flow stream and substantially absorbed by a water phase of the flow stream. The water fraction meter thus differentiates water by treating liquid hydrocarbon like gas. In the case of a liquid hydrocarbon flow stream, the infrared light is substantially transmitted through its liquid hydrocarbon phase and substantially absorbed by its water phase.

The narrow band infrared water cut meter also measures a water fraction of a multi-phase flow stream. The water cut meter includes a light source probe configured to emit an infrared light at a predetermined wavelength to a multi-phase flow stream including a first set of phases and a second set of phases whereby the infrared light is substantially transmitted through the first set of phases and substantially absorbed by the second set of phases. The water cut meter further includes a light detector probe configured to detect attenuation of the infrared light by the multi-phase flow stream whereby the attenuation indicates the water fraction of the multi-phase flow stream. In one application, the first set of phases includes a liquid hydrocarbon phase and a gas phase and the second set of phases includes a water phase.

In a fruitier application, the first set of phases includes a gas phase and a water phase and the second set of phases includes an oil phase.

BRIEF DESCRIPTION OF THE DRAWINGS

A better understanding of the present invention can be obtained when the following detailed description of the preferred embodiment is considered in conjunction with the following drawings, in which:

FIG. 4 is a schematic view of sensor components of the narrow band infrared water fraction meter of FIG. 3 in relation to a flow stream through a pipeline with portions of the pipeline broken away;

DETAILED DESCRIPTION OF THE PREFERRED EMBODIMENT

Figure 1:
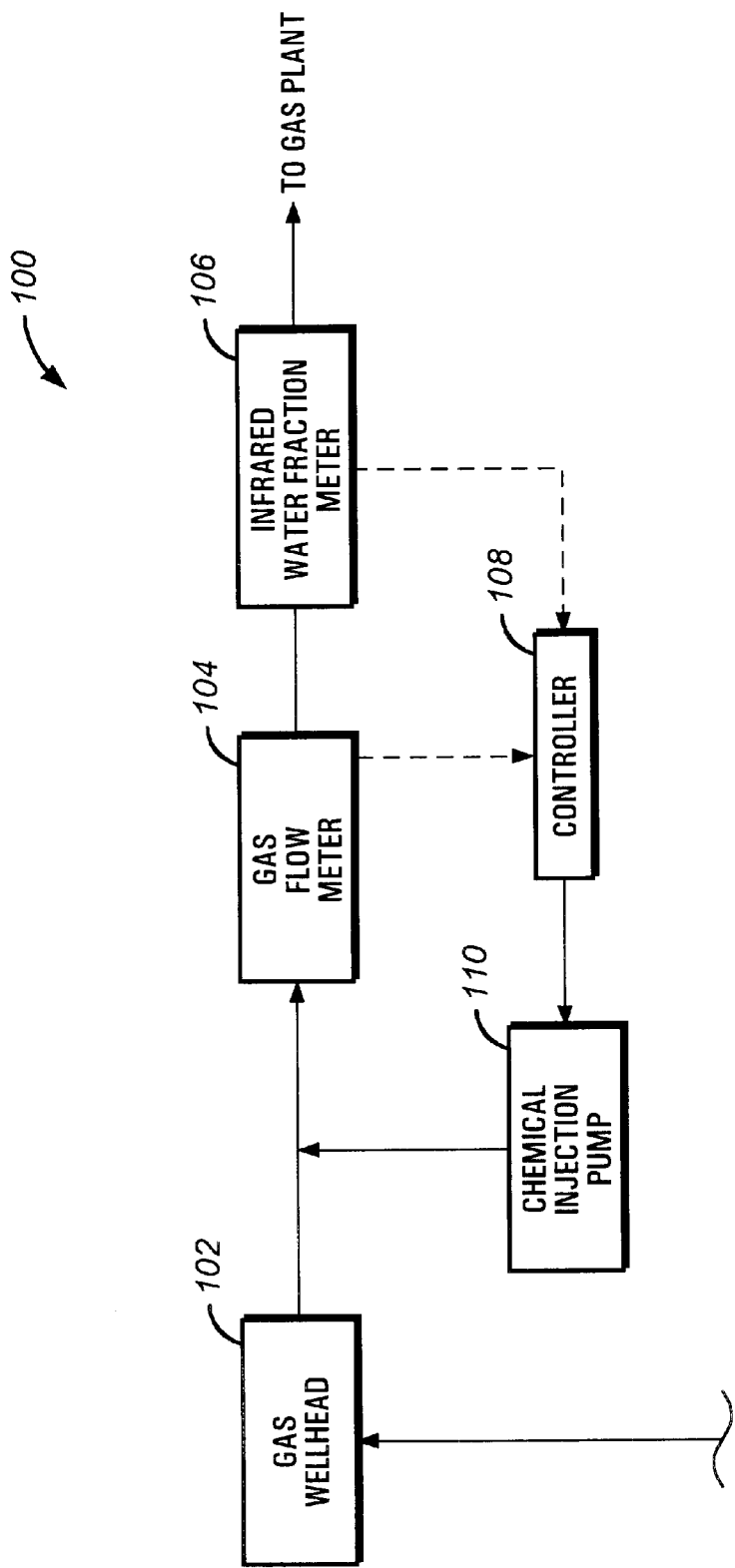
FIG. 1 is a schematic diagram of a production gas well configuration including a narrow band infrared water fraction meter.

Turning now to the drawings, FIG. 1 shows an exemplary production gas well configuration 100 employing a narrow band infrared water fraction meter 106. A flow stream is provided from a gas wellhead 102 to a gas flow meter 104. The flow stream is passed from the gas flow meter 104 to the narrow band infrared water fraction meter 106. From the water fraction meter 106, the flow stream is passed to a gas plant. As represented by the illustrated dashed lines, a controller 108 is in signal communication with the gas flow meter 104, the infrared water fraction meter 106 and a chemical injection pump 110.

It is common for gas wells to produce components other than those that are commonly thought of as "natural gas". Water, for example, is commonly produced as is carbon dioxide, hydrogen sulfide and condensate (liquid hydrocarbon). The water and the liquid hydrocarbon may represent a relatively small volume percentage of the flow stream. Often chemical agents need to be added to the production line to inhibit corrosion or hydrate formation due to the water content. The proper concentration of chemical additive is based in part on the water content of the stream. The narrow band infrared water fraction meter 106 measures the water fraction in real time, and the gas flow meter 104 measures the total volumetric flow rate. The gas flow meter 104 is commonly an orifice plate design. The controller 108 reads the signals from the gas flow meter 104 and the water fraction meter 106 and adjusts the rate of the chemical injection pump 110 to control the feed of the inhibitor chemicals into the flow stream between the gas wellhead 102 and the gas flow meter 104. A suitable controller, for example, can be obtained from manufacturers such as Modicom, Allen Bradley and Bristol Babcock. As an alternative to the use of the controller 108, the water cut from the water fraction meter 106 can be manually monitored and the chemical injection rate can be manually adjusted accordingly. Other gas well configurations employing the narrow band infrared water fraction meter 106 are possible.

Figure 2:
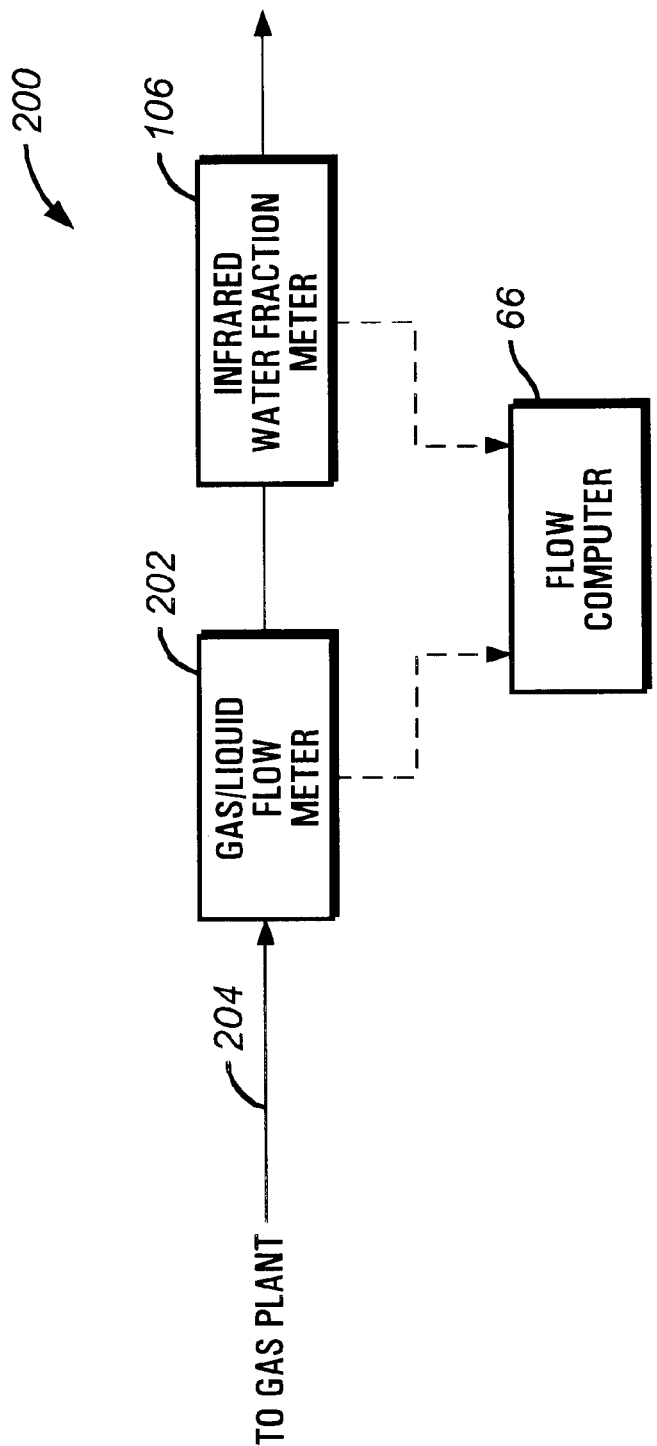
FIG. 2 is a schematic diagram of a liquid hydrocarbon pipeline configuration including a narrow band infrared water fraction meter.

Referring to FIG. 2, a pipeline configuration 200 including a gas or liquid (gas/liquid) flow meter 202 and the narrow band infrared water fraction meter 106 is shown. A pipeline 204 carries a liquid hydrocarbon-based fluid or flow stream such as crude oil or fuel where there is a potential for water contamination. The narrow band infrared water fraction meter 106 calculates the water fraction of the fluid. A flow computer 66, which is described later in connection with FIGS. 3 and 5A–5B, reads the instantaneous flow rate of the fluid provided by the gas/liquid flow meter 202 via a control signal 206 and the water cut provided by the narrow band water cut meter 106 via a control signal 208. Together this information is used to calculate the water fraction as a function of overall volume flow during a set period of time. If the water fraction exceeds a set value, then the narrow band infrared water fraction meter 106 can issue an alarm or its results can be used as the basis of accepting or rejecting a batch transfer of fluid. A control signal 206 is provided from the water fraction meter 106 back to the gas/liquid flow meter 202 for that purpose.

Thus, one disclosed application (FIG. 1) of the narrow band infrared water fraction meter 106 involves use at a gas well production header. The flow stream from the gas well 102 is passed through the water fraction meter 106, and the water content or fraction is measured. The water fraction value is then used in real time to optimize injection of corrosion inhibiting and hydrate inhibiting chemicals into the pipeline. A second application (FIG. 2) involves use of the narrow band infrared water fraction meter 106 to measure low levels of water content in a liquid hydrocarbon stream. On pipelines or at loading terminals where the transfer of liquid hydrocarbons such as crude oil or fuels takes place, water is considered a contaminant. The narrow band infrared water fraction meter 106 can detect water content as low as 100 ppm (parts per million) to help verify the integrity of liquid hydrocarbon. If the water fraction is significantly high, then the liquid hydrocarbon stream can be treated to reduce the water fraction.

Figure 3:
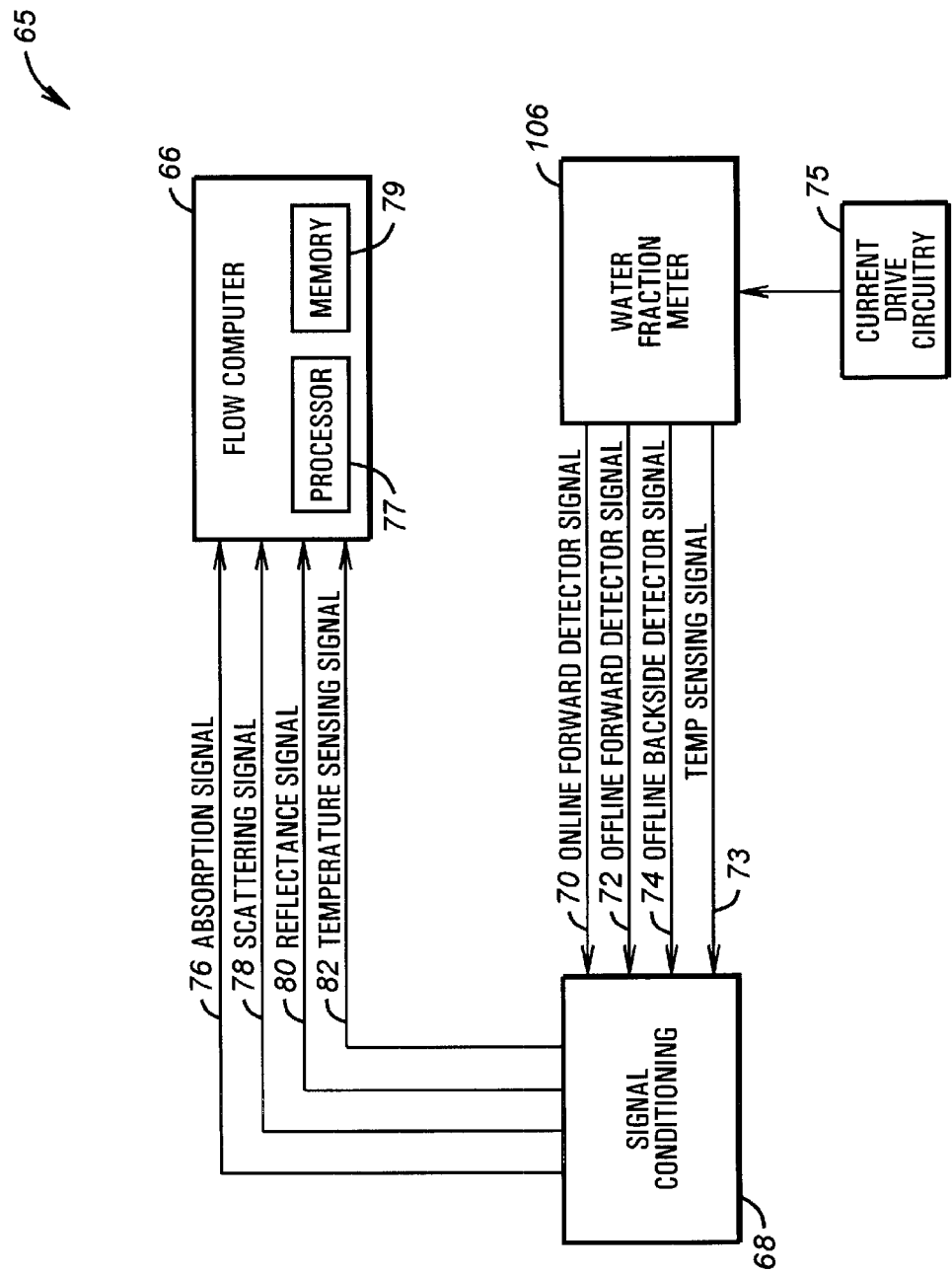
FIG. 3 is a schematic diagram of a narrow band infrared water fraction meter system including a flow computer, a narrow band infrared water fraction meter, signal conditioning block, and current drive circuitry.
Figure 9:
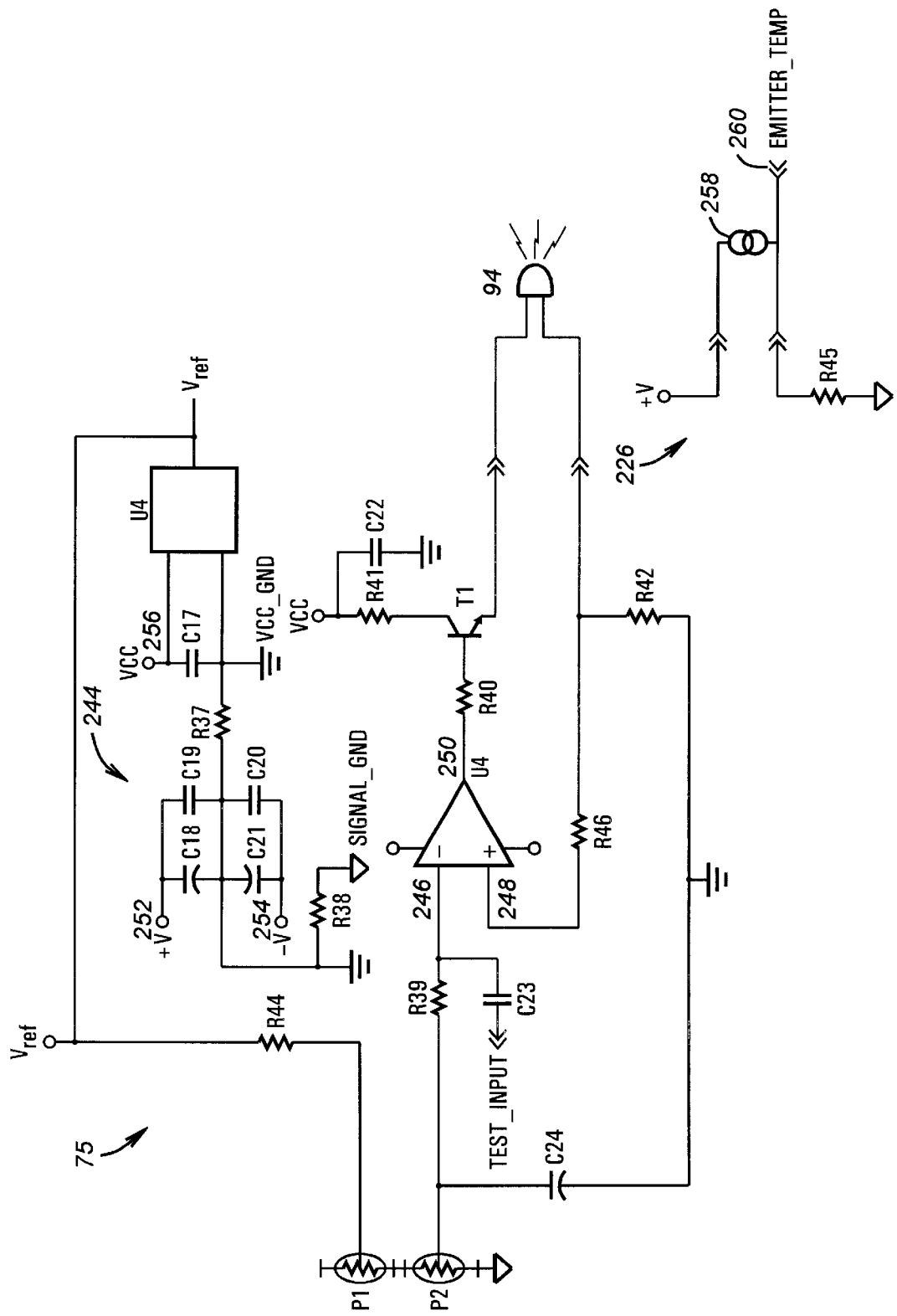
FIG. 9 is an exemplary circuit schematic of temperature sensing circuitry of FIG. 4 and the current drive circuitry of FIG. 3 for the emitter of FIG. 4.

Referring to FIG. 3, a narrow band infrared water fraction meter system 65 is shown. The narrow band infrared water fraction meter system 65 provides a flow computer 66, signal conditioning block 68, a narrow band infrared water fraction meter 106, and current drive circuitry 75. The narrow band infrared water fraction meter 106 includes the emitter 94 (FIG. 4) for emitting a narrow band of infrared light to the flow stream. The emitter 94 is driven by current drive circuitry (FIG. 9). The narrow band infrared water fraction meter 106 may include the online forward detector 96, an offline forward detector 98, and an offline backside detector 400 (FIG. 4) for detecting attenuation of the narrow band of infrared light by a flow stream. The narrow band infrared water fraction meter 106 alternatively may provide the online forward detector 96 as its single detector. In the case of a single detector configuration, the single detector preferably provides a fairly large surface area so as to measure some degree of scattering. Thus, in a single detection configuration, only absorption and scattering are measured. The online forward detector 96 produces an online forward detector signal 70 representing absorption of the narrow band of infrared light; the offline forward detector 98 produces an offline forward detector signal 72 representing "scattering" of the narrow band of infrared light; and the offline backside detector 100 produces an offline backside detector signal 74 representing "reflectance" of the narrow band of infrared light. "Scattering" generally refers to infrared light traveling in a forward direction other than by a direct path, as opposed to the technical definition of scattering. "Reflectance" generally refers to infrared light traveling in a reverse direction other than by a direct path.

The online forward detector signal 70, the offline forward detector signal 72, a temperature sensing signal 73, and the offline backside detector signal 74 are provided to the signal conditioning block 68 for conditioning (or processing) the detector signals. The signal conditioning block 68 provides an absorption signal 76, a scattering signal 78, a reflectance signal 80, and a temperature sensing signal 82 to the flow computer 66. The absorption signal 76 is the output of online forward detector signal conditioning circuitry 220 (FIG. 6); the scattering signal 78 is the output of offline forward detector signal conditioning circuitry 222 (FIG. 7); and the reflectance signal is the output of offline backside detector signal conditioning circuitry 224 (FIG. 8). The flow computer 66 is of a conventional type and serves to interpret the absorption signal 76, scattering signal 78, reflectance signal 80, and temperature sensing signal 82. The temperature sensing signal 82 is the output of the temperature sensing circuitry 226 (FIG. 9) for sensing the temperature of the emitter 94 (FIG. 4). Signals can be provided or conveyed between the optoelectronics (emitters and detectors) of the narrow band infrared water fraction meter 106 and the flow stream in a variety of ways, such as fiber optics for example.

Referring to FIG. 4, a schematic view of sensor components of the narrow band infrared water fraction meter 106 in relation to a flow stream 84 is shown. The illustrated embodiment of the narrow band infrared water fraction meter 106 includes a light source probe 90 and a light receiver probe 92. The light source probe 90 houses the emitter 94 for emitting a narrow band of infrared light to the flow stream 84 and an offline backside detector 400 for detecting "reflectance" of a narrow band of infrared light. In the illustrated example, light beams 402 and 404 are emitted by the emitter 94, and light beam 406 is detected by the offline backside detector 400. The light receiver probe 92 houses an online forward detector 96 for detecting absorption of a narrow band of infrared light and an offline forward detector 98 for detecting "scattering" of a narrow band of infrared light. In the illustrated example, light beam 402 is detected by the online forward detector 96, and the light beam 404 is detected by the offline forward detector 98. For shielding purposes, both the light source probe 90 and the light receiver probe 92 are separated from the flow stream 84 by glass windows 403 and 405 which may be sealed to the body of the probes 90 and 92. A variety of optical emitters and detectors (both light emitting diode-based components and laser-based components) are commercially available. One example of a suitable detector is a large area, high sensitivity InGaA photodiode available from Fermionics Opto-Technology of Simi Valley, Calif. One example of a suitable emitter is a light emitting diode-based emitter available from Telcom Devices Corp. of Camarillo, Calif.

The sensor components of the narrow band infrared water fraction meter 106 are preferably placed on a pipeline 83 containing the flow stream 84. The pipeline 83 is shown with portions broken away to illustrate the relationship between the flow stream 84 and the water fraction meter 106. A static mixer (not shown) may be placed upstream of the narrow band infrared water fraction meter 106 in order to mix the flow stream 84 for increasing the accuracy of measurements by the narrow band water fraction meter 106. The flow stream 84 includes continuous media 86 which is typically gas or liquid hydrocarbon and non-continuous media 88 which is typically water.

Figure 5A:
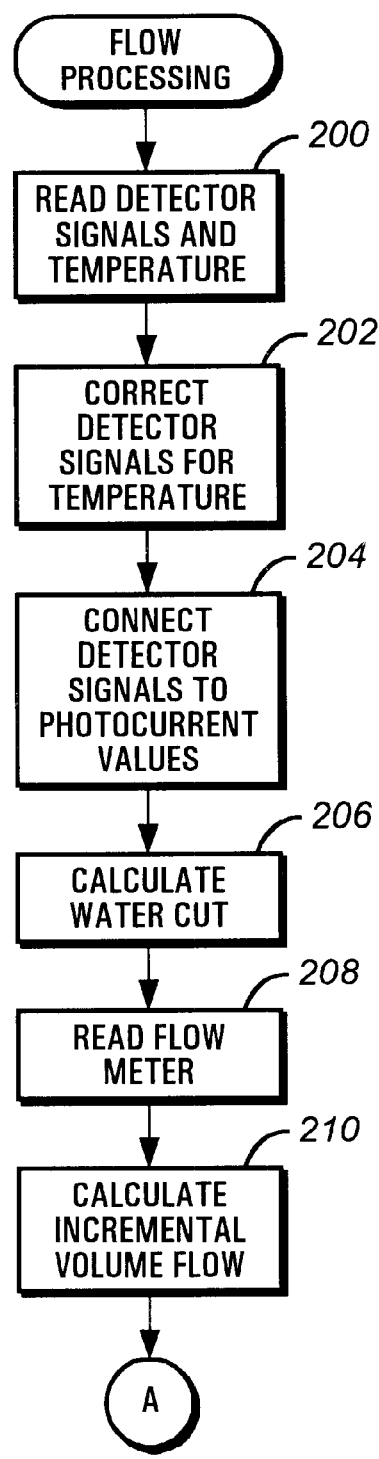
FIGS. 5A and 5B are flow charts of the flow processing technique performed by the flow computer of FIG. 3 for determining the water fraction of a flow stream with the narrow band infrared water cut meter of FIG. 3.
Figure 5B:
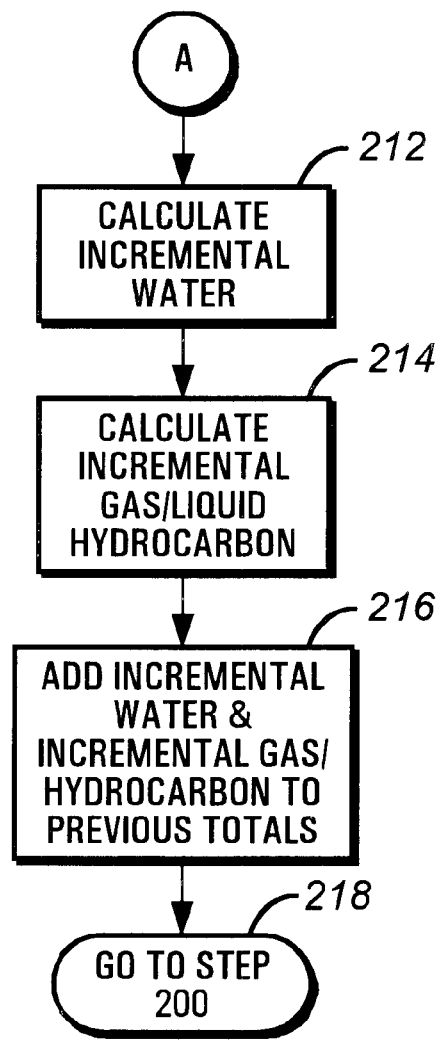

Referring to FIGS. 5A and 5B, flow charts of the flow processing technique performed by the flow computer 66 (FIG. 3) for determining water fraction with the narrow band infrared water fraction meter 106 are shown. The flow computer 66 includes a processor readable medium 79 such as a memory for storing code executed by the processor 77 to perform the flow processing technique. Control begins at step 200 where the detector signals 70, 72 and 74 and temperature sensing signal 82 are read by the flow computer 66. From step 200, control proceeds to step 202 where the detector signals are corrected for temperature of the emitter 94 provided by the temperature sensing signal 82. Following is an exemplary equation which may be used for correcting the detector signals for temperature:

$$\text{Corrected Signal} = [\text{Detector Signal}][1.2331 - 0.00303T].$$

The variable "T" in the above equation represents the temperature of the emitter 94 in degrees Fahrenheit. A temperature correction is helpful since the output of the emitter 94 varies with temperature. Next, in step 204, the corrected detector signals are converted to photocurrent values. Following is an exemplary equation which may be used for converting the corrected detector signals to photocurrent values:

$$\text{Photocurrent} = \text{Corrected Signal} \div \text{Amplified Gain Resistor}.$$

Each detector signal is associated with signal conditioning circuitry having an amplifier gain resistor. The resistance value of the amplifier gain resistor is used in the above equation for converting the detector signal to a photocurrent value. From step 204, control proceeds to step 206 where the water fraction of the flow stream 84 is calculated. The water fraction of the flow stream 84 is calculated by a non-homogeneous linear equation which includes detector photocurrent values, an absorption constant, and hardware constants. Following is an exemplary equation which may be used for calculating the water fraction ($C_W$):

$$C_W = 100 - A \, Log \, (\text{Online Forward Detector Photocurrent} + (B \cdot \text{Offline Forward Detector Photocurrent})) + C.$$

In the above equation, A represents an absorption constant determined based on a pure water absorption measurement; B represents a geometric hardware constant for the offline forward detector 98; and C represents an absorption constant determined on a pure gas or liquid hydrocarbon absorption measurement. If the backside detector photocurrent is greater than a reference backside detector photocurrent, Offline Backside Detector Photocurrent$_{ref}$, then the term D·(Offline Backside Detector Photocurrent−Offline Backside Detector Photocurrent$_{ref}$) is added to the water fraction equation. The Offline Backside Detector Photocurrent$_{ref}$ represents a photocurrent value of the offline backside detector 400 for a flow stream free of emulsions. The offline backside detector calibration constant, D, is empirically determined. Further, the water fraction, $C_W$, is a value between 0 and 100, 0 representing 0% water and 100 representing 100% water. In accordance with the disclosed techniques, a water fraction calculation is simplified by accounting for each detector signal in a single equation.

Control next proceeds to step 208 where a pulse input is measured by a gas or liquid flow meter 104 or 202 (FIGS. 1 and 2). Next, in step 210, an incremental volume flow is calculated based on the pulse input detected by the flow meter 104 or 202. From step 210, control proceeds to step 212 (FIG. 7B) where an amount of incremental water is calculated. This amount may be calculated by multiplying the incremental volume by the calculated water fraction, $C_W$. Control next proceeds to step 214 where an amount of incremental gas and/or liquid hydrocarbon (gas/liquid hydrocarbon) is calculated. The amount may be calculated by multiplying the incremental volume by (100−$C_W$%). Next, in step 216, the calculated amount of incremental gas/liquid hydrocarbon and the calculated amount of incremental water may be totaled with any previous incremental gas/liquid hydrocarbon and incremental water measurements. In step 218, control returns to step 200 where the detector signals 70, 72, and 74 and temperature sensing signal 82 are again read. The flow processing technique thus provides continuous water fraction calculations. Many modifications and variations to flow processing will be apparent to those skilled in the art.

Different flow models or regimes may be useful for flow processing depending upon the particular application. For example, in an application, where gas and water travel at different velocities or where water travels along the wall of a pipeline while gas travels along the center of the pipeline, a flow model can take these flow conditions into account. Further, where a flow model best operates based on certain flow conditions, techniques can be employed to achieve those flow conditions. For example, if a flow model best operates in the case of a homogeneous flow stream, then a nozzle can be used to mix a flow stream to obtain a homogeneous flow stream. Thus, it should be appreciated that flow data can be rendered meaningful or more meaningful in a variety of ways.

Figure 6:
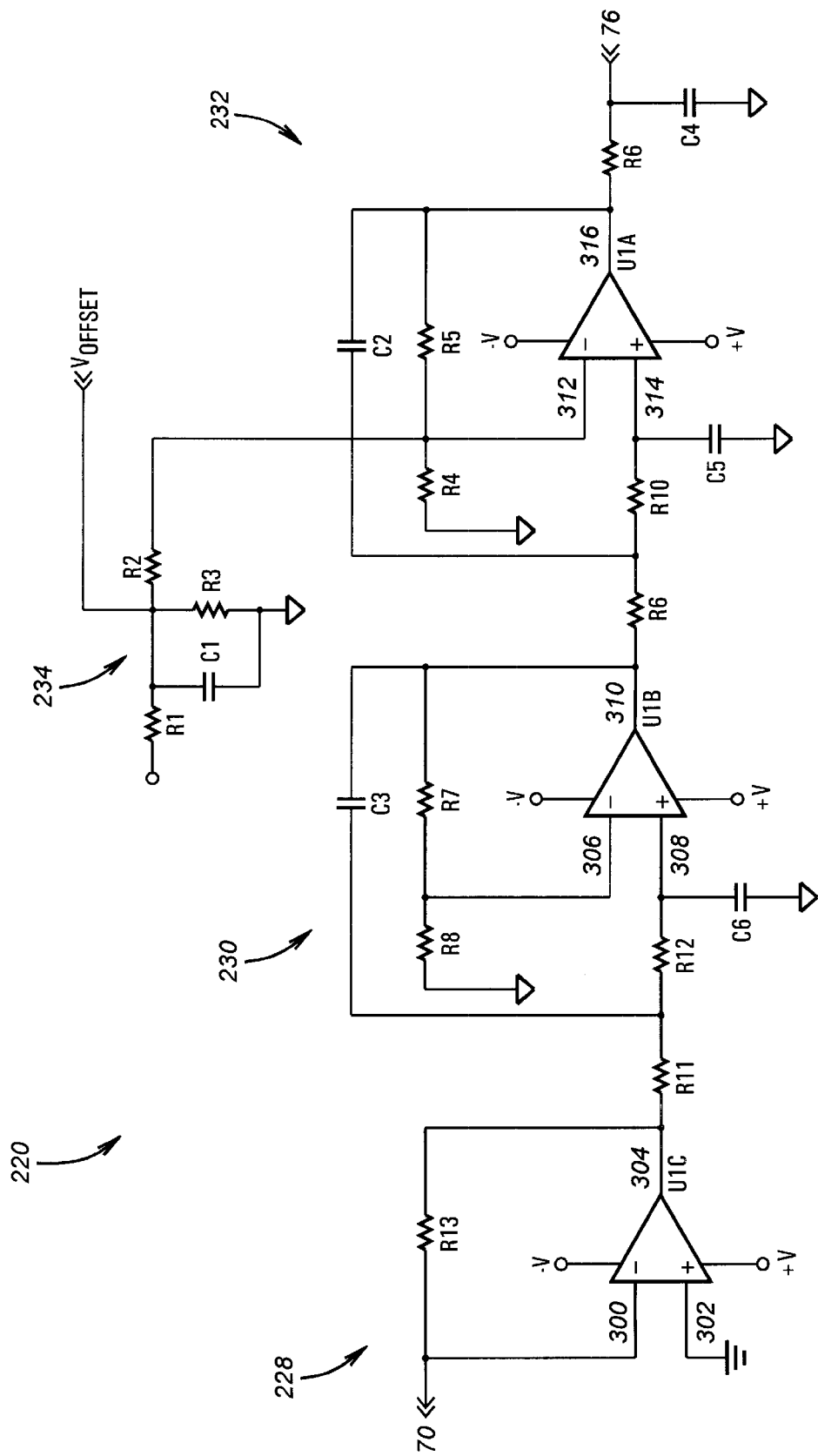
FIG. 6 is an exemplary circuit schematic of the signal conditioning circuitry of FIG. 3 for the online forward detector of FIG. 4.

The signal conditioning block 68 (FIG. 3) includes online forward detector signal conditioning circuitry 220 (FIG. 6), offline forward detector signal conditioning circuitry 222 (FIG. 7), and offline backside detector signal conditioning circuitry 224 (FIG. 8). Referring to FIG. 6, an exemplary circuit schematic of signal conditioning circuitry 220 for the online forward detector 96 is shown. The input signal to the signal conditioning circuitry 220 is the online forward detector signal 70. The online detector signal 70 is provided to an inverting terminal 300 of an operational amplifier U1C which uses current-to-voltage conversion to measure a short circuit current of the online forward detector 96. A feedback network containing a feedback resistor R13 is provided between the inverting terminal 300 and the output terminal 304 of the operational amplifier U1C. Further, the non-inverting terminal of the operational amplifier U1C is coupled to ground.

The current-to-voltage conversion stage 228 is followed by a low pass filter stage 230. In the disclosed embodiment, the low pass filter stage 230 provides a fourth order Bessel low pass filter having a gain of four in the pass band and a cutoff frequency of approximately 0.2 hertz. The illustrated embodiment of the low pass filter stage 230 includes an operational amplifier U1B and an operational amplifier U1A, both having a capacitive and resistive feedback network. The non-inverting terminal 308 of the operational amplifier U1B is coupled to a capacitor C6 and a resistor R12. The resistor R12 is series coupled to a resistor R11 which serves as a connection between the current-to-voltage conversion stage 228 and the low pass filter stage 230. The inverting terminal 306 is coupled to the common node between a feedback resistor R7 and a feedback resistor R8. Feedback resistor R8 is also coupled to ground. A feedback capacitor C3 is coupled between the output terminal 310 and the common node between resistors R11 and R12.

The non-inverting terminal 314 of the operation amplifier U1A is coupled to an input capacitor C5 and an input resistor R10. The input resistor RIO is further coupled to a resistor R9 coupled to the output terminal 310 of the operational amplifier U1B. An inverting terminal 312 of the operational amplifier U1A is coupled to a feedback network 232 and offset circuitry 234. In the disclosed embodiment, the offset circuitry 234 ensures that the output of the signal conditioning circuitry 220 does not become negative. The offset circuitry 234 includes a resistor R2 and a resistor R3 in a shunt relationship, both resistors being coupled to an offset voltage $V_{offset}$. The offset circuitry 234 further includes a resistor R1 serially coupled to the resistor R2 and a capacitor C1 in a parallel relationship with the resistor R3. Both the resistor R3 and the capacitor C1 are coupled to ground.

The feedback network 232 includes a feedback resistor R5 and a feedback resistor R4 coupled to the inverting terminal 312 of the operational amplifier U1A. The feedback resistor R4 is also coupled to ground, and the feedback resistor R5 is also coupled to the output node 316. The feedback network 232 also includes a feedback capacitor C2 coupled between the output node 316 and a node defined between resistor R9 and resistor R10. The output node 316 is further coupled to a resistor R6 which is coupled to a capacitor C4 and a node forming the output signal 76.

Figure 7:
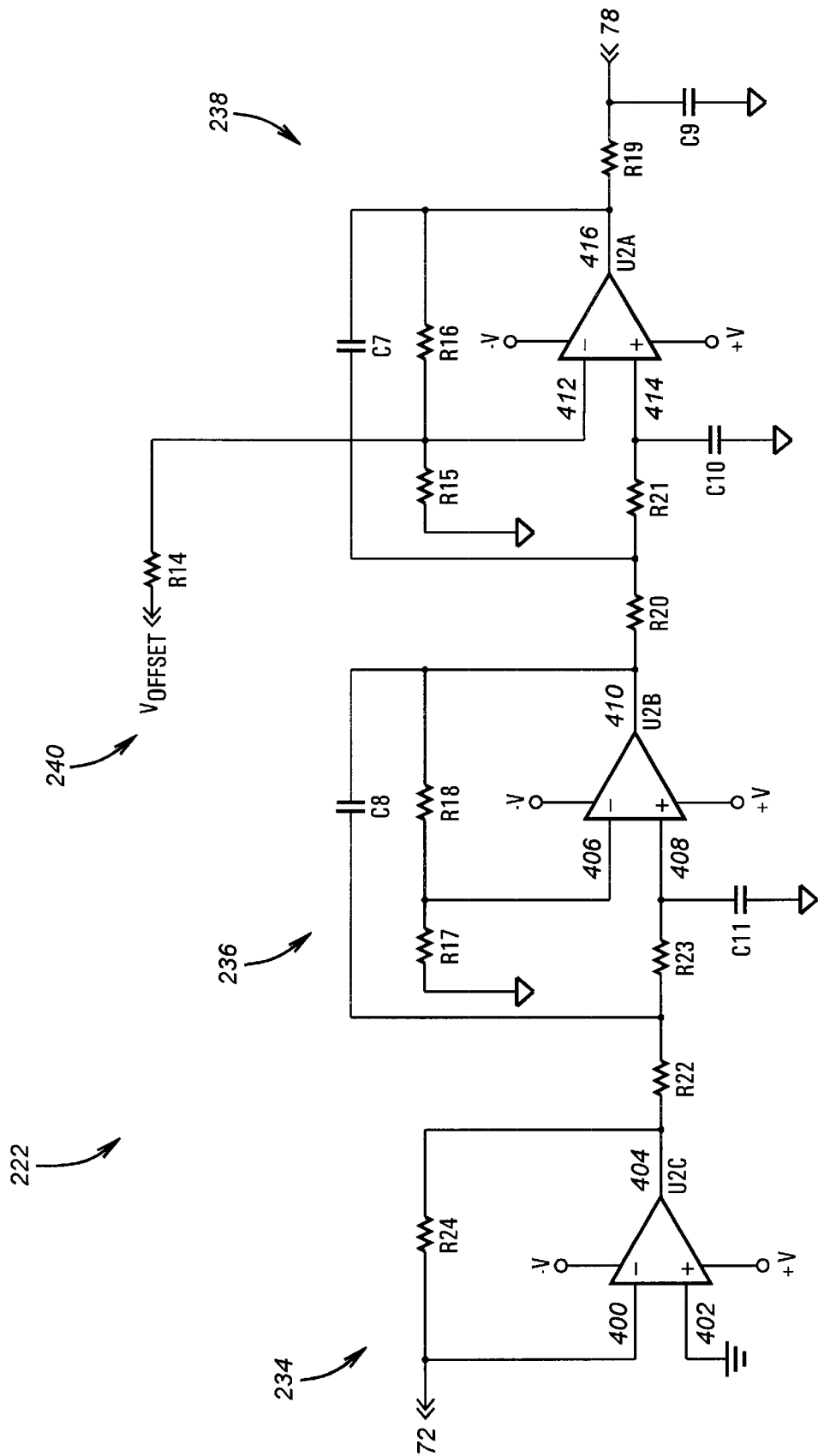
FIG. 7 is an exemplary circuit schematic of the signal conditioning circuitry of FIG. 3 for the offline forward detector of FIG. 4.
Figure 8:
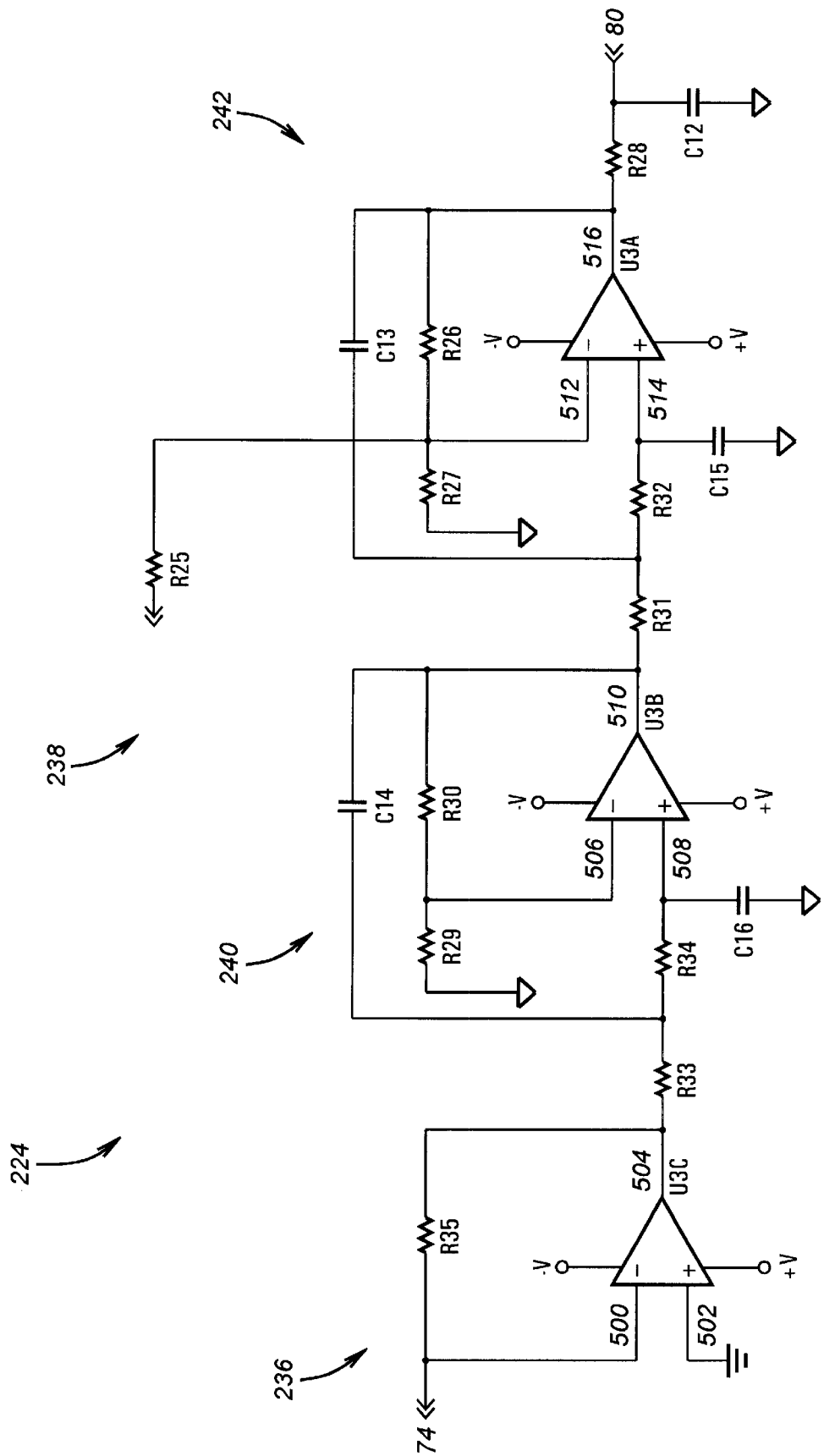
FIG. 8 is an exemplary circuit schematic of the signal conditioning circuitry of FIG. 3 for an offline backside detector of FIG. 4.

Referring to FIG. 7, an exemplary circuit schematic of signal conditioning circuitry 222 for the offline forward detector 100 is shown. The input signal to the signal conditioning circuitry 222 is the online forward detector signal 72. The online detector signal 72 is provided to an inverting terminal 400 of an operational amplifier U2C which uses current-to-voltage conversion to measure a short circuit current of the offline forward detector 100. A feedback network comprising a feedback resistor R24 is provided between the inverting terminal 400 and the output terminal 404 of the operational amplifier U2C. Further, the non-inverting terminal 402 of the operational amplifier U2C is coupled to ground.

The current-to-voltage conversion stage 234 is followed by a low pass filter stage 240. In the disclosed embodiment, the low pass filter stage 240 provides a fourth order Bessel low pass filter having a gain of four in the pass band and a cutoff frequency of approximately 0.2 hertz. The illustrated embodiment of the low pass filter stage 240 includes an operational amplifier U2B and an operational amplifier U2A, both having a capacitive/resistive feedback network. The non-inverting terminal 408 of the operational amplifier U2B is coupled to a capacitor C11 and a resistor R23. The resistor R23 is coupled to a resistor R22 which couples the current-to-voltage conversion stage 234 and the low pass filter stage 240. The inverting terminal 406 of the operational amplifier U2B is coupled to a feedback resistor R18 and a feedback resistor R17. The feedback resistor R17 is also coupled to ground. A feedback capacitor C8 is coupled between the output terminal 410 and a node defined between resistor R22 and R23.

The non-inverting terminal of the operation amplifier U2A is coupled to an input capacitor C10 and input resistor R21. The input resistor R21 is further coupled to a resistor R20 coupled to the output terminal 410 of the operational amplifier U2B. The inverting terminal 412 of the operational amplifier U2A is coupled to a feedback network 238 and also to an offset signal $V_{offset}$ through a resistor R14.

The feedback network 238 includes a feedback resistor R16 and a feedback resistor R15 coupled to the inverting terminal 412 of the operational amplifier U2A. The feedback resistor R15 is also coupled to ground, and the feedback resistor R16 is also coupled to the output node 416. The feedback network 238 also includes a feedback capacitor C7 coupled between the output node 416 and a node defined between resistor R20 and resistor R21. The output node 416 is further coupled to a resistor R19 which is coupled to a capacitor C9 and a node forming the output signal 78.

Referring to FIG. 8, an exemplary circuit schematic of signal conditioning circuitry 224 for the offline backside detector 400 is shown. The input signal to the signal conditioning circuitry 224 is the offline backside detector signal 74. The offline backside detector signal 74 is provided to an inverting terminal 500 of an operational amplifier U3C which uses current-to-voltage conversion to measure a short circuit current of the offline backside detector 400. A feedback network comprising a feedback resistor R35 is provided between the inverting terminal 500 and the output terminal 504 of the operational amplifier U3C. Further, the non-inverting terminal 502 of the operational amplifier U3C is coupled to ground.

The current-to-voltage conversion stage 236 is followed by a low pass filter stage 240. In the disclosed embodiment, the low pass filter stage 240 provides a fourth order Bessel low pass filter having a gain of four in the pass band and a cutoff frequency of approximately 0.2 hertz. The illustrated embodiment of the low pass filter stage 240 includes an operational amplifier U3B and an operational amplifier U3A, both having a capacitive and resistive feedback network. The non-inverting terminal 508 of the operational amplifier U3B is coupled to a capacitor C16 and a resistor R34. The resistor R34 is coupled to a resistor R33 which serves as a bridge between the current-to-voltage conversion stage 236 and the low pass filter stage 240. The inverting terminal 506 is coupled to a feedback resistor R30 and a feedback resistor R29. Feedback resistor R29 is also coupled to ground. A feedback capacitor C14 is coupled between the output terminal 510 and the common node of resistors R34 and R33.

The non-inverting terminal 514 of the operation amplifier U3A is coupled to an input capacitor C15 and input resistor R32. The input resistor R32 is further coupled to a resistor R31, which is also coupled to the output terminal 510 of the operational amplifier U3B. The inverting terminal 512 of the operational amplifier U1A is coupled to a feedback network 242 and also to an offset voltage, $V_{offset}$, through resistor R25.

The feedback network 242 includes a feedback resistor R26 and a feedback resistor R27 coupled to the inverting terminal 512 of the operational amplifier U3A. The feedback resistor R27 is also coupled to ground, and the feedback resistor R26 is also coupled to the output node 516. The feedback network 242 also includes a feedback capacitor C13 coupled between the output node 516 and a node defined between resistor R31 and resistor R32. The output node 516 is further coupled to a resistor R28 which is coupled to a capacitor C12 and a node forming the output signal 80. Many modifications and variations to signal processing will be apparent to those skilled in the art.

Referring to FIG. 9, an exemplary circuit schematic of current drive circuitry 75 for the emitter 94, temperature sensing circuitry 226, and power decoupling circuitry 244 is shown. The current drive circuitry 75 essentially provides a voltage-to-current circuit for driving the emitter 94. In the disclosed embodiment, the current drive circuitry 75 includes a pair of potentiometers P1 and P2, an operational amplifier U4 configured as a voltage-to-current converter, a transistor T1, and the emitter 94. The potentiometer P1 is connected to a register R44 coupled to a reference voltage $V_{ref}$. The potentiometer P2 is coupled to a capacitor C24 and a resistor R39. The resistor R39 is connected to a capacitor C23 coupled to an inverting terminal 246 of the operational amplifier U4 and to a test input signal, TEST_INPUT, used for detecting a frequency response. A non-inverting terminal 248 is coupled to a resistor R46 which is coupled to a resistor R42 and the emitter 94. In the disclosed embodiment, the emitter 94 is a light emitting diode for converting current to infrared light. The resistor R42 and the capacitor C24 are further coupled to a power supply ground VCC_GND. The output terminal 250 of the operational amplifier U4 is coupled to a resistor R40, which is coupled to a base of the transistor T1. In the disclosed embodiment, the transistor T1 is a bipolar junction transistor. The collector of the transistor T1 is coupled to a resistor R41 which is coupled to a capacitor C22. The capacitor C22 is further coupled to a power supply ground VCC_GND. The emitter of the transistor T1 is coupled to the emitter 94 of the narrow band water fraction meter 32. In the disclosed configuration, the transistor T1 thus serves as a current controlled switch, and the current drive circuitry 75 drives the emitter 94 with a current proportional to the voltage influenced by the potentiometers P1 and P2.

The power decoupling circuitry 244 is of a conventional type having advantages appreciated by one of ordinary skill in the art. In the disclosed embodiment, a +5V power supply and a +15V power supply are provided. In the disclosed embodiment of the power decoupling circuitry 244, an input node 252, which is a positive terminal of a +15V power supply, is coupled to a capacitor C18 and a capacitor C19 having a parallel relationship. Both the capacitor C18 and the capacitor C19 are further coupled to a capacitor C21 and a capacitor C20. The capacitors C21 and C20 are coupled to another input node 254, which is a negative terminal of a +15V power supply. Capacitor C18 and capacitor C21 are coupled to a resistor R38 which couples the 15V power supply ground VCC_GND to the signal ground SIGNAL_GND. The capacitor C19 and capacitor C20 are further coupled to a resistor R37. The resistor R37 couples the 15V power supply ground to the 5V power supply ground. Capacitor C17 has a parallel relationship with the voltage $V_{ref}$ and is coupled to a node 256, which is the positive terminal of the +15V power supply.

The temperature sensing circuitry 226 is used for sensing the temperature of the emitter 94. In the disclosed embodiment, the temperature sensing circuitry 226 includes a temperature sensor 258 which is coupled to a resistor R45. An output terminal 260 of the circuit is coupled to the temperature sensor 258 and the resistor R45. The output terminal 260 provides an output signal EMITTER_TEMP, representing the temperature of the emitter 94. The resistor R45 is further coupled to a signal ground SIGNAL_OGND.

Figure 10:
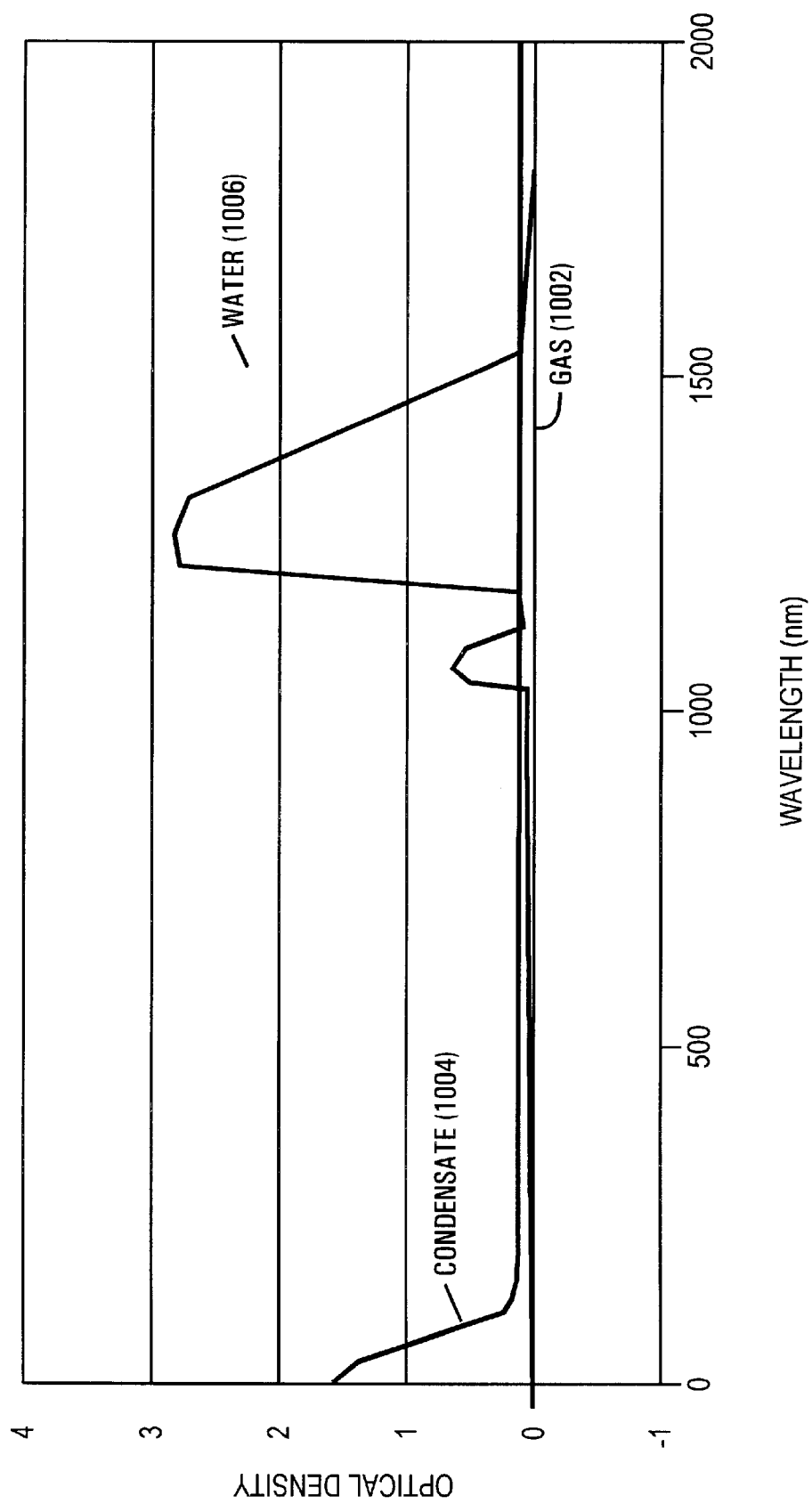
FIG. 10 is a graph diagram illustrating the transmission properties of oil and water for a near to mid infrared region including a narrow infrared band in which light is emitted by the narrow band infrared water fraction meter of FIG. 3.

Referring to FIG. 10, a graph diagram illustrating the optical density or spectral properties of water, gas and condensate (liquid hydrocarbon) for a section of the near infrared region including a narrow infrared band in which light is emitted by the narrow band infrared water fraction meter 106 is shown. The optical density characteristics of water, gas and condensate for the illustrated wavelength range are represented by signal patterns 1006, 1002 and 1004. The emitter 94 of the narrow band infrared water fraction meter 106 emits a narrow band of infrared light selected from the near infrared region. In one embodiment of the narrow band infrared water fraction meter 106, a wavelength is selected at which the optical density characteristic of water is substantially different from the optical density characteristic of natural gas. The selected wavelength thus provides for differentiation of gas content and water content of the flow stream. Further, at the selected wavelength, the optical density characteristic of condensate (liquid hydrocarbon) is essentially the same as the optical density characteristic for gas as represented by the close proximity of signal patterns 1004 and 1002 at certain wavelengths. Thus, at the selected wavelength, the narrow band infrared water fraction meter 106 does not confuse condensate for water. It has been found that at a wavelength on the order of approximately 1450 nanometers, the optical density characteristic for water 1006 is substantially different from the optical density characteristic for gas 1002. For example, at approximately 1450 nanometers in the illustrated diagram, the optical density curve for water which is in the 2–3 optical density range has a substantially greater percentage of infrared signal optical density than the optical density curve for gas which is close to 0 optical density. It should be understood that wavelengths in the near to mid infrared region having a like effect to a wavelength of 1450 nanometers may also be selected.

Figure 11:
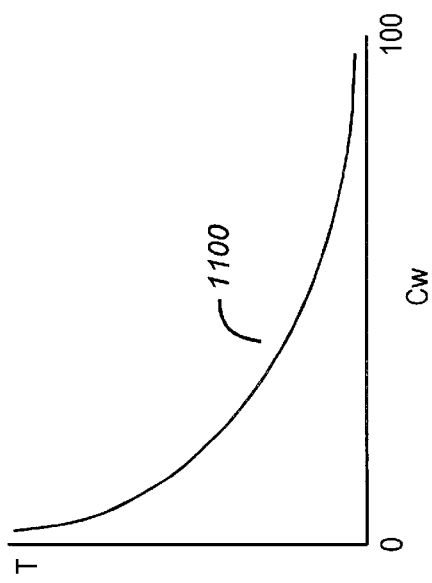
FIG. 11 is a graph diagram illustrating signal transmission for a detector of the narrow band infrared water cut meter of FIG. 3 as a function of the water fraction of the flow stream of FIG. 3.

Referring to FIG. 11, a graph diagram illustrating signal transmission for a detector of the narrow band infrared water fraction meter 106 as a function of the water fraction $C_w$ of the flow stream is shown. A transmission curve 1100 represents the logarithmic relationship between the water fraction Cw of the flow stream and transmission T by a detector signal of the narrow band infrared water fraction meter 106 over a fill water fraction range.

Figure 12:
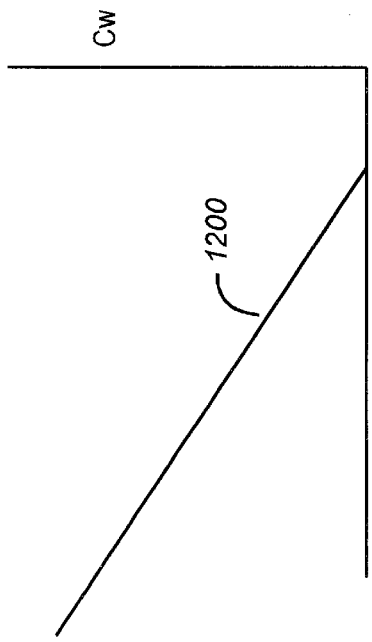
FIG. 12 is a graph diagram illustrating an exemplary water fraction of a flow stream as a function of the logarithm of signal transmission for a detector of the narrow band infrared water fraction meter of FIG. 3.

Referring to FIG. 12, a graph diagram illustrating water fraction $C_W$ of the flow stream as a function of a logarithm of signal transmission T for a detector of the narrow band infrared water fraction meter 106 is shown. Like FIG. 11, the linear water fraction curve 1200 of FIG. 12 serves to illustrate the logarithmic relationship between transmission T for a detector signal of the narrow band infrared water fraction meter 106 and the water fraction $C_W$ of the flow stream. The slope of the water fraction curve 1200 corresponds to the A calibration constant value, and the vertical axis intercept value of the curve 1200 corresponds to the C calibration constant value.

Figure 13:
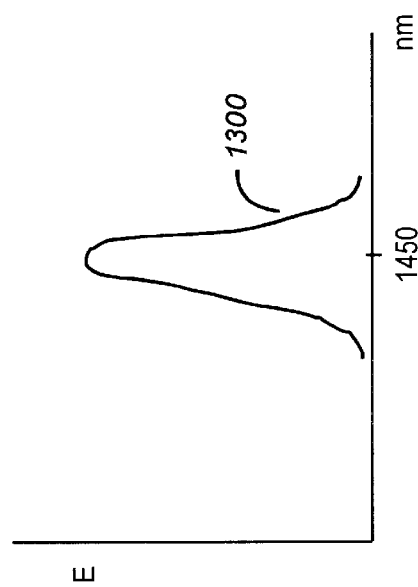
FIG. 13 is a graph diagram illustrating an exemplary light emission by the emitter of FIG. 4 over an exemplary wavelength range.

Referring to FIG. 13, a graph diagram illustrating an exemplary light emission by the emitter 94 over an exemplary wavelength range is shown. The light emission 1300 is centered at a wavelength of approximately 1450 nanometers. The light emission 1300 can represent a narrow band of light which is substantially transmitted through gas content and condensate content of a flow stream and is substantially absorbed by water content of the flow stream. The light emission 1300 can also represent a narrow band of light which is substantially transmitted through a liquid hydrocarbon phase of a flow stream and substantially absorbed by a water phase of the flow stream.

Thus, the narrow band infrared water fraction meter 106 provides for a full range water fraction detection independent of entrained condensate for a host of applications. It should be understood that the applications described herein are exemplary and not exhaustive. For example, another application would be providing the narrow band water fraction meter 106 downhole as a module in a sensing package or apparatus suitable for downhole water fraction measurements, eliminating the need to separate the flow stream for testing at the surface. Further, it should be understood that the location, placement, position, or environment of the narrow band water fraction meter 106 or any of its components may be varied.

Further, the narrow band water fraction meter essentially can be configured to measure a water fraction of a multiphase flow stream. The emitted light is substantially transmitted through one set of phases and substantially absorbed by a second set of phases.

Either set of phases may include one or more phases. In one application, the infrared light is substantially transmitted through a gas phase and a liquid hydrocarbon phase and substantially absorbed by a water phase. In another application, the infrared light is substantially transmitted through a liquid hydrocarbon phase and substantially absorbed by a water phase.

The foregoing disclosure and description of the various embodiments are illustrative and explanatory thereof, and various changes in the size, shape, materials, components, circuit elements, wiring connections and contacts, as well as in the details of the illustrated circuitry and construction and method of operation may be made without departing from the spirit of the invention.

We claim:

1. A method of measuring a water phase of a flow stream of a gas well, the flow stream including a gas phase, a liquid hydrocarbon phase and a water phase, the method comprising the steps of:

directing the flow stream to an infrared water fraction meter;

emitting a narrow band of infrared light by the infrared water fraction meter at a predetermined wavelength whereby the infrared light is substantially transmitted through the gas phase and the liquid hydrocarbon phase and substantially absorbed by the water phase; and detecting attenuation of the infrared light with the infrared water fraction meter whereby the attenuation indicates the water fraction of the flow stream.

2. The method of claim 1, further comprising the step of:
   controlling injection of corrosion/hydrate inhibiting chemicals into the flow stream based on the attenuation of the infrared light detected in the detecting step.

3. The method of claim 1, wherein the water phase and the liquid hydrocarbon phase represent a relatively small volume percentage of the flow stream.

4. The method of claim 1, wherein the predetermined wavelength is approximately 1450 nanometers.

5. A method of measuring a water phase of a liquid hydrocarbon flow stream including a water phase and a liquid hydrocarbon phase, the method comprising the steps of:

directing the liquid hydrocarbon flow stream to an infrared water fraction meter;

emitting a narrow band of infrared light by the infrared water fraction meter at a predetermined wavelength whereby the infrared light is substantially transmitted through the liquid hydrocarbon phase and substantially absorbed by the water phase; and detecting attenuation of the infrared light by the infrared water fraction meter whereby the attenuation indicates the water fraction of the liquid hydrocarbon flow stream.

6. The method of claim 5, wherein the liquid hydrocarbon phase comprises fuel.

7. The method of claim 5, further comprising the step of:

treating the liquid hydrocarbon flow stream to reduce the water fraction of the liquid hydrocarbon flow stream based on the attenuation of the infrared light detected in the detecting step.

8. A method of measuring a multi-phase flow stream using an infrared water fraction meter, the method comprising the steps of:

directing a multi-phase flow stream to an infrared water fraction meter;

emitting a narrow band of infrared light by the infrared water fraction meter at a predetermined wavelength whereby the infrared light is substantially transmitted through a first set of phases of the multi-phase flow system and substantially absorbed by a second set of phases of the multi-phase flow stream; and detecting attenuation of the infrared light by the infrared water fraction meter whereby the attenuation indicates the water fraction of the multi-phase flow stream.

9. The method of claim 8, wherein the first set of phases comprises a water phase and the second set of phases comprises a liquid hydrocarbon phase and a gas phase.

10. The method of claim 8, wherein the first set of phases comprises a gas phase and a water phase and the second set of phases comprises an oil phase.

11. An infrared water fraction meter configured to measure a water phase of a flow stream of a gas well, the meter comprising:

a light source probe configured to emit a narrow band of infrared light at a predetermined wavelength to a flow stream including a gas phase, a liquid hydrocarbon phase and a water phase whereby the infrared light is substantially transmitted through the gas phase and the liquid hydrocarbon phase and substantially absorbed by the water phase; and a light detector probe configured to detect attenuation of the infrared light by the flow stream whereby the attenuation indicates the water fraction of the flow stream.

12. The water fraction meter of claim 11, wherein the predetermined wavelength is approximately 1450 nanometers.

13. An infrared water fraction meter configured to measure a water fraction of a multi-chase flow stream, the meter comprising:

a light source probe configured to emit a narrow band of infrared light at a predetermined wavelength to a multi-phase flow stream including a first set of phases and a second set of phases whereby the infrared light is substantially transmitted through the first set of phases and substantially absorbed by the second set of phases; and a light detector probe configured to detect attenuation of the infrared light by the multi-phase flow stream whereby the attenuation indicates the water fraction of the multi-phase flow stream.

14. The water fraction meter of claim 13, wherein the first set of phases comprises a liquid hydrocarbon phase and a gas phase and the second set of phases comprises a water phase.

15. The water fraction meter of claim 13, wherein the first set of phases comprises a water phase and a gas phase and the second set of phases comprises an oil phase.

16. An infrared water fraction apparatus configured to measure a water phase of a flow stream of a gas well, the apparatus comprising:

a light emitter means for emitting a narrow band of infrared light at a predetermined wavelength to a flow stream including a gas phase, a liquid hydrocarbon phase and a water phase whereby the infrared light is substantially transmitted through the gas phase and the liquid hydrocarbon phase and substantially absorbed by the water phase; and a light detector means for detecting attenuation of the infrared light by the flow stream whereby the attenuation indicates the water fraction of the flow stream.

17. The water fraction apparatus of claim 16, wherein the predetermined wavelength is approximately 1450 nanometers.

18. An infrared water fraction apparatus configured to measure a multi-phase flow stream the apparatus comprising:

a light emitter means for emitting a narrow band of infrared light at a predetermined wavelength to the multi-phase flow stream including a first set of phases and a second set of phases whereby the infrared light is substantially transmitted through the first set of phases and substantially absorbed by the second set of phases; and a light detector means for detecting attenuation of the infrared light by the multi-phase flow stream whereby the attenuation indicates the water fraction of the multi-phase flow stream.

19. The water fraction apparatus of claim 18, wherein the first set of phases comprises a liquid hydrocarbon phase and a gas phase and the second set of phases comprises a water phase.

20. The water fraction apparatus of claim 18, wherein the first set of phases comprises a water phase and a gas phase and the second set of phases comprises an oil phase.

* * * * *

UNITED STATES PATENT AND TRADEMARK OFFICE
CERTIFICATE OF CORRECTION

PATENT NO.    : 6,292,756 B1
DATED         : September 18, 2001
INVENTOR(S)   : John S. Lievois et al.

It is certified that error appears in the above-identified patent and that said Letters Patent is hereby corrected as shown below:

<u>Column 13,</u>
Line 59, please delete the word "multi-chase" and replace with the word -- multi-phase. --

Signed and Sealed this

Twenty-first Day of May, 2002

Attest:

Attesting Officer

JAMES E. ROGAN
*Director of the United States Patent and Trademark Office*